United States Patent [19]
Khanna et al.

[11] Patent Number: 5,919,642
[45] Date of Patent: Jul. 6, 1999

[54] COMPETITIVE BINDING ASSAYS HAVING IMPROVED LINEARITY

[75] Inventors: Pyare Khanna, Fremont; William A. Coty, Davis; Dean Jenkins, Castro Valley, all of Calif.

[73] Assignee: Boehringer Mannheim Corporation, Indianapolis, Ind.

[21] Appl. No.: 08/946,891

[22] Filed: Oct. 8, 1997

Related U.S. Application Data

[63] Continuation-in-part of application No. 08/358,322, Dec. 19, 1994, abandoned.

[51] Int. Cl.$^6$ .................. G01N 33/536; G01N 33/542
[52] U.S. Cl. ................. 435/7.9; 435/7.6; 435/7.93; 435/962; 436/536; 436/537
[58] Field of Search ................ 435/7.6, 7.9, 7.93, 435/18, 817, 962; 436/536, 537; 204/403

[56] References Cited

U.S. PATENT DOCUMENTS

| | | | |
|---|---|---|---|
| 4,378,428 | 3/1983 | Farina et al. ................ | 435/7.9 |
| 4,600,690 | 7/1986 | Karmen et al. ............... | 435/7 |
| 4,708,429 | 11/1987 | Henderson .................. | 435/7.6 |
| 4,785,080 | 11/1988 | Farina et al. . | |
| 4,830,959 | 5/1989 | McNeil et al. . | |
| 4,912,041 | 3/1990 | Batchelor et al. . | |
| 4,950,612 | 8/1990 | Khanna et al. . | |
| 4,956,274 | 9/1990 | Khanna et al. . | |
| 4,963,245 | 10/1990 | Weetall . | |
| 5,032,503 | 7/1991 | Khanna et al. . | |
| 5,037,735 | 8/1991 | Khanna et al. . | |
| 5,106,950 | 4/1992 | Farina et al. . | |
| 5,120,653 | 6/1992 | Henderson . | |
| 5,124,253 | 6/1992 | Foulds et al. . | |
| 5,202,233 | 4/1993 | Herrmann et al. . | |
| 5,212,081 | 5/1993 | Coty et al. . | |
| 5,229,282 | 7/1993 | Yoshioka et al. . | |
| 5,427,912 | 6/1995 | Brown et al. ............... | 435/7.6 |
| 5,444,161 | 8/1995 | Manning et al. . | |
| 5,470,713 | 11/1995 | El Shami et al. ............ | 435/7.72 |

FOREIGN PATENT DOCUMENTS

| | | |
|---|---|---|
| 0125139 | 11/1984 | European Pat. Off. . |
| 0150999 | 8/1985 | European Pat. Off. . |
| 0327312 | 8/1989 | European Pat. Off. . |
| 0328380 | 8/1989 | European Pat. Off. . |
| 0350808 | 1/1990 | European Pat. Off. . |
| 0546536 | 6/1993 | European Pat. Off. . |
| 95/06115 | 3/1995 | European Pat. Off. . |
| WO 86/03837 | 7/1986 | WIPO . |
| WO 86/04926 | 8/1986 | WIPO . |
| WO 90/13569 | 11/1990 | WIPO . |
| WO 91/16630 | 10/1991 | WIPO . |

OTHER PUBLICATIONS

Shaw et al. "Linearization of Data for Saturation–type Competitive Protein Binding Assay and Radioimmunoassay" *Clinica. Chimica, ACTA* (1977) 76(1):15–24.

E. T. Maggio, Enzyme–Immunoassay, CRC Press, Inc., 1980, pp. 106–107.

NR Rose et al (eds) "Manual of Clinical Laboratory Immunology" 3d ed, (1986), American Society for Microbioloby (Washington D.C.), pp. 89–98.

Declaration by William A. Coty.

Product insert and related information—Gentamicin CEDIA® assay.

Product insert and related information—Theophylline CEDIA® assay.

Product insert and related information—Tobramycin CEDIA® assay.

Product insert and related information—N–acetylprocainamide CEDIA® assay.

Gil et al., "Competitive heterogeneous enzyme immunoassay for theophyline by flow–injection analysis with electrochemical detection of ρ–aminophenol" *Clin. Chem.* (1990) 36(4):662–665.

Jenkins et al., "Extending the detection limit of solid–phase electrochemical enzyme immunoassay to the attomole level" *Anal. Biochem.* (1988) 168:292–299.

Jenkins et al., "The use of ion pairing reagents to reduce non–specific adsorption in a solid phase electrochemical enzyme immunoassay" *Contributed Article* (1990) 13(2):99–104.

Thompson et al., "Comparison of methods for following alkaline phosphatase catalysis: spectrophotometric versus amperometric detection" *Anal. Biochem.* (1991) 192:90–95.

Wright et al., "Sequestration electrochemistry: the interaction of chlorpromazine and human orosomucoid" *Anal. Biochem.* (1988) 171:290–293.

Xu et al., "Heterogeneous enzyme immunoassay of alpha–fetoprotein in material serum by flow–injection amperiometric detection of 4–aminophenol" *Clin. Chem.* (1990) 36(11):1941–1944.

*Primary Examiner*—David Saunders
*Attorney, Agent, or Firm*—Morrison&Foerster LLP

[57] ABSTRACT

Simplified calibration and improved dose-response linearity of the standard curve of competitive assays are obtained by adding a predetermined amount of unlabeled competitive binding compound (usually just the analyte itself) to a first reagent containing anti-analyte antibodies before the reagent is reacted with a sample containing an unknown amount of analyte.

4 Claims, 2 Drawing Sheets

COMPETITIVE BINDING ASSAYS HAVING IMPROVED LINEARITY

REFERENCE TO RELATED APPLICATIONS

This application is a continuation-in-part of U.S. Ser. No. 08/358,322, filed Dec. 19, 1994, abandoned. The aforelisted application is hereby incorporated herein by reference in its entirety.

FIELD OF THE INVENTION

This invention relates to competitive immunoassays having simplified calibration and improved dose-response linearity of their standard curves.

BACKGROUND

Numerous immunoassays using the competitive binding principle have been developed to determine the amount of biologically or medically relevant chemicals or proteins (e.g., enzymes, hormones, blood proteins) in a sample. Processing of data and reporting of results in immunoassays is of obvious importance when determining the fundamental differences in the nature of dose-response relations for certain biologicals in a sample. Assay results are often calculated by determining where an analytical value (such as an absorbance) falls on a "standard curve" prepared using known concentrations of analytes.

Generally, assays of the competitive type (as contrasted with immunometric or reagent excess methods) give nonlinear dose-response curves. The shape of the curve is dictated by the mass-action principle and the affinties of antibody for analyte and label. As a result, construction of an accurate standard curve requires testing of multiple standards which requires significant technician time, rigorous quality control, and high consumption of generally costly reagents. While various mathematical models can improve the precision of curve fitting to obtain accurate results with less data required for a standard curve, mathematical fitting of nonlinear standard curves requires a computer and complex software or microprocessors interfaced with detection instruments, as well as extensive mathematical transformations of the data. Inaccuracy can result from poor fit of the mathematically fitted standard curve to the actual data, especially where nonlinear standard curves exhibit poor precision and sensitivity at or near analytically critical medical decision points.

Thus, a method for producing linear standard curves in competitive assays that (1) uses only two standards, (2) eliminates use of complex mathematical curve-fitting procedures, and (3) provides more consistent precision across the range of analyte concentrations, would be a great improvement over techniques currently in use. Such a method would present clear qualitative and linear quantitative information by a reproducible method of data processing and reduce the opportunity for errors that result from transformation of response curves (i.e. compression of errors with apparent improvement of data), errors from linear interpolation between points, or errors that result from assumption of linearity.

SUMMARY OF THE INVENTION

The present invention provides a method for determining the amount of an analyte present in a sample that provides a linear dose-response curve for competitive binding assays, especially those for which a linear dose-response curve was not previously available. The method comprises (a) forming a mixture in a reaction medium by combining the sample and one or more reagents containing an anti-analyte antibody, a labeled form of the analyte being detected, and a preselected quantity or predetermined amount (less than the amount expected to be present in a typical sample) of the analyte or a competitive binding compound in unlabeled form; (b) incubating the resulting mixture to allow the binding reaction(s) to take place; and (c) measuring the amount of bound or unbound labeled analyte. The amount of unlabeled analyte or competitive binding compound added to the mixture in the reaction medium is selected to be sufficient to provide a linear standard curve (or at least improve the linearity of the curve) formed by plotting measured labeled analyte versus the concentration of analyte in the sample. Detection can be by measurement of enzyme activity, fluorescence, or any other detectable signal appropriate to the nature of the label, and the invention can be used with any competitive binding assay, either homogeneous or heterogeneous. The predetermined amount of unlabeled analyte or competitive binding compound is that amount which increases the linearity of a structural curve over a range of expected values relative to such standard curve in the absence of the unlabeled analyte or competitive binding compound. Such amount can be determined empirically as described herein using techniques known in the art.

BRIEF DESCRIPTION OF THE DRAWINGS

The invention will be better understood by reference to the following detailed description of the invention when considered in combination with the drawings that form part of the specification, wherein.

DESCRIPTION OF SPECIFIC EMBODIMENTS

Figure 1:
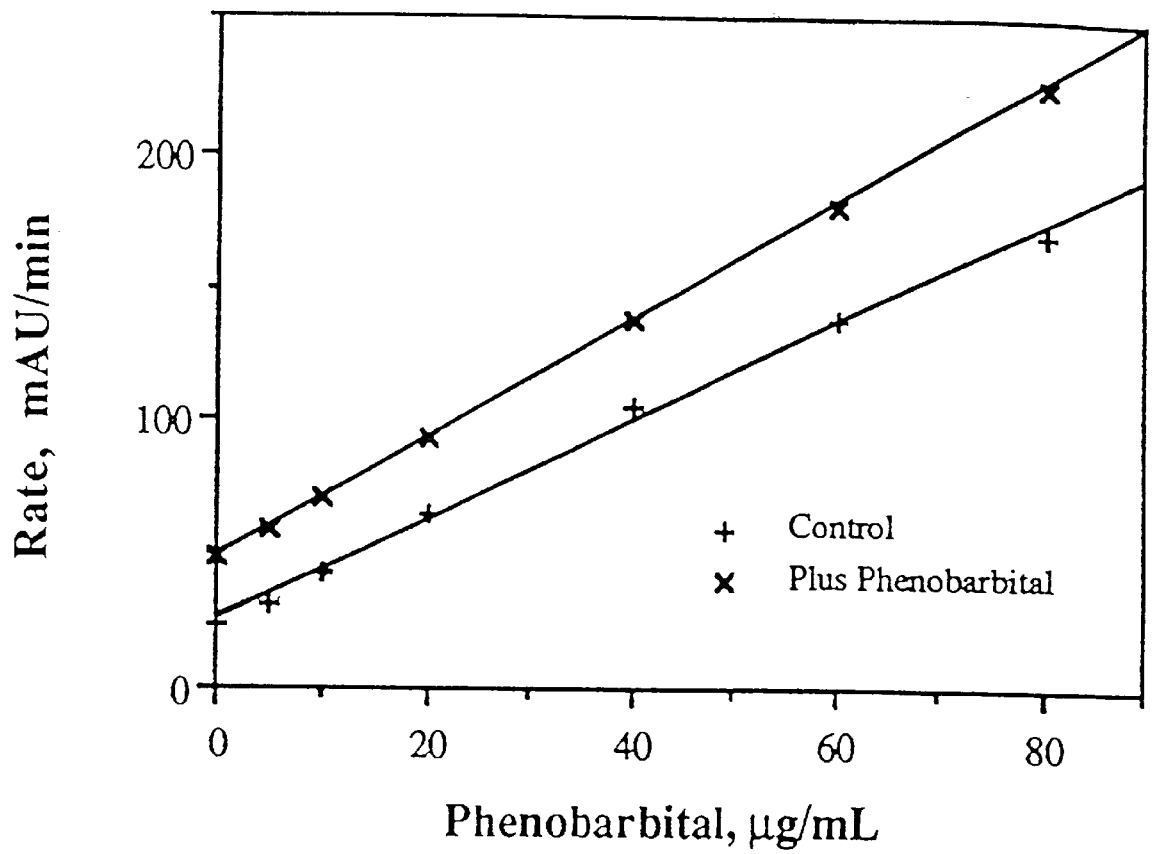
FIG. 1 is a graph showing the result of adding phenobarbital to Reagent 1 in Example 1.

The present invention simplifies the calibration and improves the dose-response linearity of a competitive binding assay by adding an effective amount of the analyte compound (or a structurally similar compound that competes with the analyte for binding to an anti-analyte antibody) to an immunoassay reagent mixture (or to one or more of the reagents if the reagents are provided separately) prior to contacting the reagent or reagents with the sample. By testing the method of the invention in actual assays at different sample dosages, it has been found that a slightly to severely nonlinear standard curve can be effectively linearized at least in those regions of the standard curve where medically important decisions are being made.

This method is applicable to any competitive binding assay, using either heterogeneous or homogeneous methods, with one or more reagents, and with all labels and detection methods known to the art. For example, detection methods may include radioactive methods; enzyme techniques using intact enzymes of many types including, for example, β-galactosidase, glucose 6-phosphate dehydrogenase, alkline phosphatase, horseradish peroxidase, or glucose oxidase; techniques using enzyme fragments, such as β-galactosidase complementation assays; detection systems including chromogenic substrates; fluorescent methods detected by direct fluorescence, time-resolved fluorescence, fluorescence polarization, or fluorescence energy transfer; and chemi- or bioluminescence detection systems. This method can be used to quantify any analyte that can be determined by competitive binding assay methods.

The process of the invention can be used with any competitive binding assay, including those in which the analyte is a therapeutic drug (e.g., phenobarbital, gentamicin, digoxin), a hormone (e.g., estriol, thyroxine, insulin), a drug or pharmaceutical of abuse (e.g., morphine, amphetamine), a metabolite (e.g., benzoylecgonine), or a serum protein (e.g., IgG, C-reactive protein).

As used herein, an "analyte" is the specific chemical or biochemical compound or other material whose presence or amount is being determined by analysis.

A "sample" is the source material that contains (or, in negative samples, is suspected of containing) the analyte and is usually but not necessarily of biological origin, although pretreatment may have removed some of the normal biological compounds normally associated with the analyte (such as red cells separated from plasma in a whole blood sample).

A "competitive binding assay" uses competition between an analyte and a different molecule, called the competitive binding compound, for a limited number of binding sites on a specific binding molecule, usually an antibody, to determine whether, or how much of, an analyte is present.

An "anti-analyte antibody" is an antibody that binds with an analyte by a specific binding association, which typically but not necessarily has an association constant of at least $10^8$. The antibody is "specific" for the particular analyte of interest if the analyte binds to the antibody in preference to any other compound expected to be present in the same sample. Other specific binding compounds that are not antibodies (such as, for example, lectins, which bind specific carbohydrates) can be used in competitive binding assays in the same manner as antibodies. However, since the wording required to enumerate all such compounds would unnecessarily add to the complexity of this description without adding to the understanding of one skilled in the art, the phrase "anti-analyte" antibody as used herein is intended to encompass all such specific binding compounds.

A "competitive binding compound" is a compound that competes with the analyte for binding to the anti-analyte antibody and can be the analyte molecule itself or a structurally related analog or derivative of the analyte that retains ability to bind to the antibody or the specific binding molecule. Thus, the term "competitive binding compound" as used herein also encompasses compounds other than "analytes"; it includes both analytes and molecules that compete with analyte for binding to anti-analyte antibody. A "labeled competitive binding compound" also comprises a detectable label common to competitive binding assays (discussed in detail below). An "unlabeled competitive binding compound" does not have the label being detected in the particular assay being used, although it may be detectable by other techniques.

A compound is a "derivative" of a first compound (as used herein for preferred embodiments) if the derivative compound is formed (or can be formed) by reaction of the first compound with another molecule or reagent so as to form a new compound either smaller or larger than the first compound while retaining at least part of the structure of the first compound.

A "moiety" is a part of a complex derivative molecule that is derived from the indicated original moiety. For example, the "analyte moiety" of a analyte/label complex molecule is the part of the complex originally derived from a whole analyte molecule.

By "standard curve" as used herein is meant a sample dose-response curve based on a curved or substantially linear line drawn to connect at least two sample dosage data points corresponding to individual sample dose analyses. Curved lines are present for assays having nonlinear dose response curves over the range of sample analyte values. This invention provides a method wherein satisfactory results for an assay that relies on a standard curve can be achieved by drawing a straight line using only two data points from the expected range of analyte concentrations in a sample.

In one embodiment of the invention, a first reagent containing anti-analyte antibody and a preselected (i.e., predetermined) amount of unlabeled analyte or an unlabeled competitive binding compound is reacted with a sample containing an unknown amount of the analyte to form a first reaction mixture. This mixture is incubated (usually at 25° C. to 42° C.; preferably at 37° C.) to allow binding and a second reagent containing labeled analyte or labeled competitive binding compound is added and the incubation is continued to allow further binding reactions to occur. Subsequently, a third reagent is added that precipitates the anti-analyte antibody and whatever has bound to it. Examples of the third reagent include any of the numerous precipitating reagents used in heterogeneous assays, such as second antibodies (i.e., antibodies against the first anti-analyte antibody). The mixture is separated by centrifugation, and the amount of labeled analyte in either the precipitate or the supernatant fraction is measured. The reagents can contain any useful additional ingredients, such as solvents, buffers, stabilizers (e.g., ethylenediaminetetraacetic acid, 2-mercaptoethanol, and the like), bactericides, surface-active agents, and the like. The form of label and detection method are not limited, as is described above. Some labeling/detection methods (e.g., enzyme label) will require addition of a further reagent such as an enzyme substrate to allow detection.

In this embodiment, analyte in the sample competes with labeled analyte for a limited number of anti-analyte antibody binding sites. As the amount of analyte in the sample increases, the amount of labeled analyte recovered in the precipitate decreases, while the amount of labeled analyte recovered in the supernatant fraction increases. Either measurement can be used to construct a standard curve of labeled analyte recovered versus analyte concentration in the sample; this standard curve can be used to quantify analyte present in unknown samples.

In assays that use this type of competition in the absence of the added analyte that is required in this embodiment of the invention, the dose-response curve is often concave upward at low analyte concentrations, leading to poor sensitivity and precision at low analyte concentrations. Addition of unlabeled analyte or unlabeled competitive binding compound to the anti-analyte antibody first reagent eliminates the initial curvature of the standard curve, resulting in a linear standard curve.

Alternative embodiments include homogeneous methods, e.g., where the first reagent contains enzyme substrate, anti-analyte antibody, and unlabeled analyte or competitive binding compound and the second reagent contains an enzyme-analyte conjugate. In such embodiments, analyte from the sample and enzyme-labeled conjugate compete for a limited number of anti-analyte antibody binding sites. As the amount of analyte in the sample increases, the amount of enzyme bound to antibody decreases, resulting in increased enzyme activity, since binding of antibody to the enzyme-analyte conjugate inhibits enzyme activity. The enzyme activity is measured photometrically as the rate of photometrically detectable end-product produced by chemical reaction of the enzyme with its substrate. As in the first example, addition of unlabeled analyte or unlabeled competitive binding compound to the anti-analyte containing first reagent eliminates the initial curvature of the standard curve, resulting in a linear standard curve.

A third embodiment utilizes enzyme fragments as labels for a homogeneous enzyme immunoassay. Enzyme fragments useful as labels have been disclosed in U.S. Pat. No. 4,708,929, which is herein incorporated by reference. Two enzyme fragments, referred to as enzyme donor and enzyme acceptor, have little or no enzyme activity when present in a sample separately but can combine together to restore enzyme activity (referred to as complementation). In this embodiment, the first reagent contains enzyme acceptor, anti-analyte antibody, and unlabeled analyte or unlabeled competitive binding compound, and the second reagent contains enzyme donor-analyte conjugate and an enzyme substrate. Analyte from the sample and enzyme donor-analyte conjugate compete for a limited number of anti-analyte antibody binding sites. As the amount of analyte in the sample increases, the amount of enzyme donor bound to antibody decreases. The enzyme donor is thus free to combine with enzyme acceptor to produce active β-galactosidase, which is measured photometrically as the rate of detectable end-product produced by hydrolysis of the chromogenic enzyme substrate. As in the prior embodiments, the addition of unlabeled analyte or an unlabeled competitive binding compound to the anti-analyte antibody first reagent eliminates the initial curvature of the standard curve, resulting in a linear standard curve.

The unlabeled analyte can be added to the first reagent during formulation or manufacture. The optimum amount is determined empirically by carrying out a series of assays using different, increasing amounts of the unlabeled analyte or unlabeled competitive binding compound in the reaction medium in test samples where the amount of analyte in the sample is known, and preparing a series of standard dose-response curves. The increasing amounts of unlabeled analyte or competitive binding compound tested will approach a maximum, the amount equivalent to the known analyte test amount. The optimum amount of unlabeled analyte or unlabeled competitive binding compound is the amount most effective in linearizing the standard curve over the region where linearity is desired. The optimum amount can vary depending on the physical and chemical properties of the analyte, the range of concentrations of the analyte expected to be present in the sample, the properties of the anti-analyte antibody (e.g., affinity of binding to analyte and labeled analyte), the nature of the other ingredients used in the immunoassay, and the type of assay method used. Although the optimum amount cannot be determined with absolute accuracy in the absence of the empirical testing described above, preliminary experiments varying the concentration of labeled analyte/competitive binding compound can readily be performed to determine the amount of unlabeled analyte that will improve the linearity of the standard curve in any specific immunoassay. This invention covers use of any amount of unlabeled analyte or competitive binding compound that is added to make the standard curve for an assay more linear, including the optimum amount that maximizes the linear nature of the dose-response curve and lesser than optimum amounts that simply improve linearity.

By way of nonlimiting illustration, when the analyte is gentamicin (and the assay is an homogeneous enzyme complementation assay of the type described above), the amount of unlabeled gentamicin added to the first reagent will be sufficient to provide a molar ratio of gentamicin to anti-gentamicin monoclonal antibody of from about 0.05:1 to 50:1, preferably from about 0.5:1 to 10:1, and especially from about 2:1 to 6:1.

The assay method can be used with any aqueous sample containing analyte. Other than the removal of particulates, no pretreatment of samples will usually be performed for the purposes of the invention, although pretreatment can occur for other purposes. The amount of sample can vary, but will usually comprise at least 1% to 12% of the volume of the total reaction mixture.

The invention now being generally described, the same will be better understood by reference to the following examples which are for the purposes of illustration and are not to be considered limiting of the invention unless so specified.

EXAMPLES

Example 1

Phenobarbital Assay

The data described below and illustrated in FIG. 1 were obtained with the following reagents:

1. Reagent 1 contained 5.3 nM conjugate (ED28-di [phenobarbital-1-carboxypropyl-ethylenediamine-] maleimidobenzoyl-succinimide]), 1.4 mg/mL m-cyanonitrophenyl-beta-β-galactopyranoside (Molecular Probes), and 0.8% by volume anti-phenobarbital monoclonal antibody (Kallestad Diagnostics) as ascites fluid in a buffer containing 400 mM sodium chloride, 60 mM potassium phosphate, 10 mM EGTA, 2 mM magnesium acetate, 0.05% TWEEN-208 (registered of ICI Americas, Inc. for polyoxyethylene sorbitan), and 20 mM sodium azide, pH 6.9. Where indicated in Table I below, 0.24 μg/mL phenobarbital was also added to Reagent 1 to illustrate the present invention.

2. Reagent 2 contained 467 units/mL EA22 and 4.7% by volume goat anti-mouse IgG (BiosPacific) in a buffer containing 400 mM sodium chloride, 60 mM potassium phosphate, 10 mM EGTA, 2 mM magnesium acetate, 0.05% TWEEN-20 and 20 mM sodium azide, pH 6.9.

Assay protocol

The phenobarbital assay was carried out on a HITACHI 704 clinical analyzer (Boehringer Mannheim Corp., Indianapolis, Ind.), using the following steps:

1. Four (4) μL of sample (phenobarbital test amounts in human serum) were added to each cuvette.

2. Two hundred (200) μL of Reagent 1 were added to each cuvette.

3. The reaction was carried out for 5 minutes at 37° C., with mechanical mixing at approximately 40 seconds after Reagent 1 addition.

4. One hundred fifty (150) μL of Reagent 2 were added to each cuvette.

5. The reaction was carried out for 4.5 minutes at 37° C., with mechanical mixing at approximately 40 seconds after Reagent 2 addition.

6. Four measurements of absorbance at 415 nm were taken at 20 second intervals between 4.5 and 5.5 minutes after Reagent 2 addition. Secondary absorbance measurements were also taken at a wavelength of 660 nm, and the difference between absorbance at 415 nm and 660 nm was calculated.

7. The rate of substrate hydrolysis was calculated by the Hitachi analyzer as the change of net absorbance (A415 nm minus A660 nm) per minute, using least squares regression fit of the four absorbance measurements.

Results

FIG. 1 shows the effect on curve linearity of adding phenobarbital to Reagent 1. Without phenobarbital, the standard curve linearity (the correlation coefficient "r" calculated by least squares regression analysis) was only 0.9981, whereas with phenobarbital, the correlation coefficient was 0.99996. Also, the addition of phenobarbital dramatically reduced the inaccuracy of analyte interpolation using a two-point calibration, as shown in Table 1 illustrated below. Thus, without phenobarbital in Reagent 1, samples containing 5, 20, and 40 μg/mL phenobarbital would have been measured inaccurately (errors greater than 10% and 1.0 μg/mL) using a 2-point standard curve, while with the indicated amount of phenobarbital in the reagent, all errors were substantially less than 10% and 0.5 μg/mL.

TABLE I

Effect of Phenobarbital on Accuracy of 2-Point Standard Curve

| Phenobarbital Present in Sample μg/mL | No Phenobarbital in Reagent 1 | | | With Phenobarbital in Reagent | | |
|---|---|---|---|---|---|---|
| | Measured μg/mL | Phenobarbital Error μg/mL | Error % | Measured μg/mL | Phenobarbital Error μg/mL | Error % |
| 0 | 0.00 | | | 0.00 | | |
| 5 | 3.96 | 1.04 | 20.7% | 4.58 | 0.42 | 8.4% |
| 10 | 10.18 | −0.18 | 1.8% | 9.52 | 0.48 | 4.8% |
| 20 | 22.37 | −2.37 | 11.9% | 19.91 | 0.09 | 0.5% |
| 40 | 44.69 | −4.69 | 11.7% | 40.41 | −0.41 | 1.0% |
| 60 | 62.55 | −2.55 | 4.3% | 59.95 | 0.05 | 0.1% |
| 80 | 80.00 | | | 80.00 | | |

Example II—Gentamicin Assay

The data described below and illustrated in FIG. 2 were obtained with the following reagents:

1. Reagent 1 contained 154 units/mL EA22 and 0.05% by volume anti-gentamicin monoclonal antibody (Beckman) as ascites fluid in a buffer containing 400 mM sodium chloride, 100 mM 3-N-morpholinopropanesulfonic acid (MOPS), 10 mM EGTA, 2 mM magnesium acetate, 0.05% TWEEN-20, and 20 mM sodium azide, pH 6.9. Where indicated below in Table II, gentamicin was also added to Reagent 1 at the indicated concentrations.

2. Reagent 2 contained 2.13 nM conjugate (ED 28-di[gentamicin-benzoylhomocysteine-bis-maleimidohexane]), 2.36 mg/mL chlorophenol red-beta-β-galactopyranoside (Boehringer Mannheim Biochemicals), and 2.4% by volume goat anti-mouse IgG (BiosPacific) in a buffer containing 400 mM sodium chloride, 100 mM MOPS, 10 mM EGTA, 2 mM magnesium acetate, 0.05% TWEEN-20, and 20 mM sodium azide, pH 6.9.

Assay protocol

The gentamicin assay was carried out on a HITACEH 704 clinical analyzer using the following steps:

1. Four (4) μl of sample (gentamicin test amounts in human serum) were added to each cuvette.

2. Two hundred (200) μL of Reagent 1 were added to each cuvette.

3. The reaction was carried out for 5 minutes at 37° C., with mechanical mixing at approximately 40 seconds after Reagent 1 addition.

4. One hundred fifty (150) μL of Reagent 2 were added to each cuvette.

5. The reaction was carried out for 4.5 minutes at 37° C., with mechanical mixing at approximately 40 seconds after Reagent 2 addition.

6. Four measurements of absorbance at 570 nm were taken at 20 second intervals between 4.5 and 5.5 minutes after Reagent 2 addition. Secondary absorbance measurements were also taken at a wavelength of 660 nm, and the difference between absorbance at 570 nm and 660 nm was calculated.

7. The rate of substrate hydrolysis was calculated by the HITACHI analyzer as the change of net absorbance (A570 nm minus A660 nm) per minute, using least square regression fit of the four absorbance measurements.

Results

Figure 2:
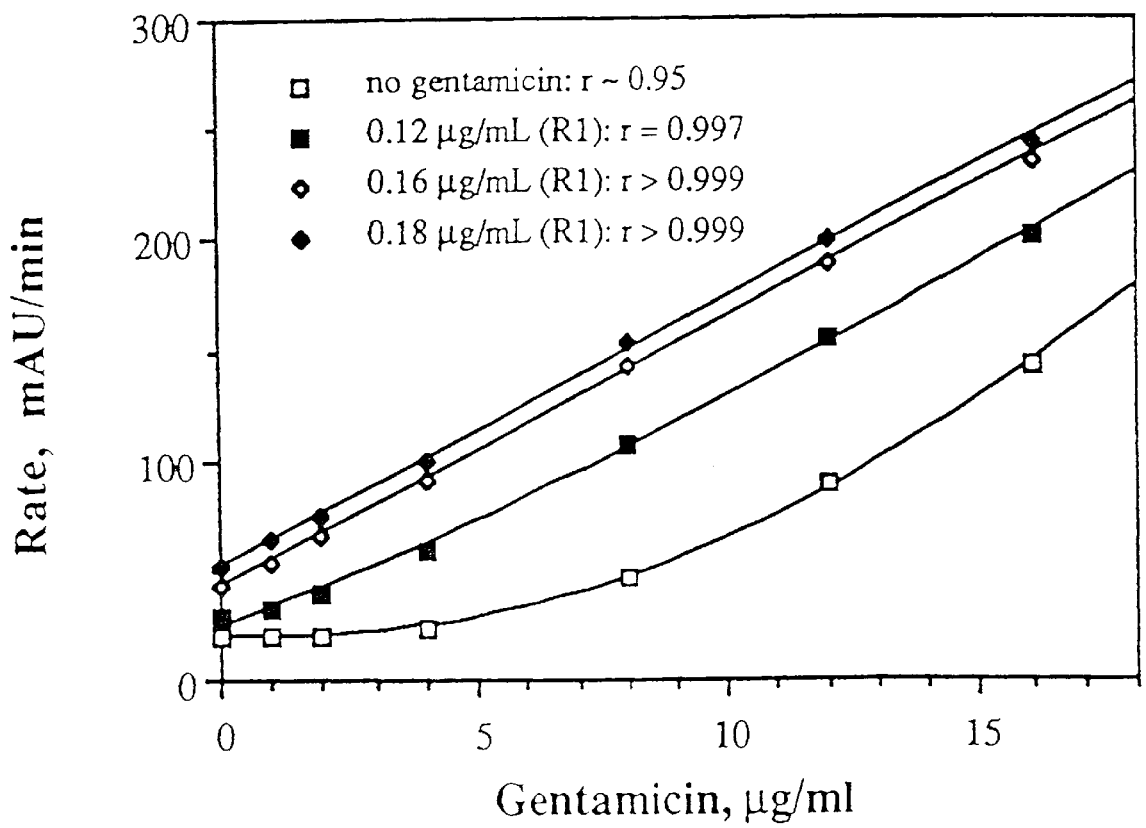
FIG. 2 is a graph showing the result of adding gentamicin to Reagent 1 in Example 2.

FIG. 2 below shows the effect on curve linearity of adding gentamicin to Reagent 1. Without gentamicin, the standard curve was severely nonlinear (r=0.95). As the gentamicin concentration was increased, the standard curve became more linear, and at a concentration of 0.16 to 0.18 μg/mL in Reagent 1, the curve exhibited a correlation coefficient of 0.999 or greater.

TABLE II

Effect of Gentamicin on Accuracy of 2-Point Standard Curve

| | Gentamicin in Reagent 1, μg/mL | | | |
|---|---|---|---|---|
| | none | 0.12 | 0.16 | 0.18 |
| Expected Value μg/mL | Measured Value μg/mL | | | |
| 0 | 0 | 0 | 0 | 0 |
| 1 | 0.03 | 0.35 | 0.90 | 0.99 |
| 2 | 0.01 | 0.96 | 2.02 | 1.93 |
| 4 | 0.43 | 2.79 | 4.01 | 3.94 |
| 8 | 3.35 | 7.28 | 8.29 | 8.42 |
| 12 | 8.96 | 11.76 | 12.20 | 12.37 |
| 16 | 16.00 | 16.00 | 16.00 | 16.00 |
| Expected Value μg/mL | Dose Error μg/mL | | | |
| 1 | −0.97 | −0.65 | −0.10 | −0.01 |
| 2 | −1.99 | −1.04 | 0.02 | −0.07 |
| 4 | −3.57 | −1.21 | 0.01 | −0.06 |
| 8 | −4.65 | −0.72 | 0.29 | 0.42 |
| 12 | −3.04 | −0.24 | 0.20 | 0.37 |
| % Error | Dose Error % | | | |
| 1 | −97.38 | −64.65 | −10.19 | −1.20 |
| 2 | −99.35 | −52.09 | 1.04 | −3.72 |
| 4 | −89.20 | −30.23 | 0.21 | −1.41 |
| 8 | −58.10 | −8.95 | 3.64 | 5.29 |
| 12 | −25.37 | −2.02 | 1.66 | 3.05 |

The abbreviations used in the Examples have the following meanings:

EGTA=Ethylene glycol-bis-(β-amino ethyl ether)N,N,B', N'-tetraacetic acid

EA 22=Enzyme acceptor #22 (U.S. Pat. No. 4,708,929)

MOPS=3-(N-morpholino)propanesulfonic acid

Any and all publications mentioned in this specification are herein incorporated by reference to the same extent as if each individual publication was specifically and individually indicated to be incorporated by reference.

The invention now being fully described, it will be apparent to one of skill in the art that many changes and modifications can be made thereto without departing from the spirit or scope of the appended claims.

What is claimed is:

1. A method for providing an improved homogeneous competitive binding assay for quantifying an analyte in a sample, wherein the steps of the assay method comprise the following:
   a) preparing a reaction mixture comprising the sample and a plurality of reagents; wherein the plurality of reagents includes:
   a labeled competitive binding compound,
   an antibody specific for the analyte, and an aqueous solvent; and
   b) measuring the amount of labeled competitive binding compound bound to the antibody in the reaction mixture as a measure of the amount of the analyte in the sample; wherein the improvement comprises including in the plurality of reagents a predetermined amount of unlabeled competitive binding compound, wherein, upon addition to the reaction mixture, the predetermined amount still permits the analyte in the sample to bind the antibody, and improves the linearity of the relationship between the amount of analyte present in the sample and the amount of analyte measured in step b); and wherein the steps of the method for providing the improved assay comprise the following:
   i) conducting the assay with samples containing varying known amounts of the analyte in the sample in the absence of any additional unlabeled competitive binding compound in the reaction mixture;
   ii) calculating the linearity of the relationship of the assay in step i) between the known amount of the analyte in the sample and the amount of analyte measured in step b) of the assay;
   iii) conducting the assay with samples containing varying known amounts of the analyte in the sample in the presence of a fixed amount of unlabeled competitive binding compound in the reaction mixture;
   iv) calculating the linearity of the relationship of the assay in step iii) between the known amount of the analyte in the sample and the amount of analyte measured in step b) of the assay;
   v) selecting the fixed amount of unlabeled competitive binding compound in step iii) as the predetermined amount for inclusion in the plurality of reagents in the improved assay if the linearity calculated in step iv) is improved in comparison with the linearity calculated in step ii).

2. The method according to claim 1, wherein the assay is conducted at a plurality of fixed amounts of reagent analyte in the reaction mixture according to step iii), and the predetermined amount selected in step v) is a fixed amount of reagent analyte giving better linearity than other fixed amounts tested.

3. The method according to claim 1, wherein the least squares regression correlation coefficient between the actual amount of analyte in the sample and the amount of analyte determined in the sample in step b) of the improved assay is 0.999 or greater.

4. The method according to claim 1, wherein the plurality of reagents in the improved assay contains a molar ratio of unlabeled competitive binding compound:antibody of between about 2:1 and 6:1.

* * * * *